(12) United States Patent
Brunnberg et al.

(10) Patent No.: US 8,875,700 B2
(45) Date of Patent: Nov. 4, 2014

(54) DOSE INFORMATION DEVICE

(75) Inventors: Lennart Brunnberg, Tyresö (SE); Stephan Olson, Stockholm (SE); Anders Wieselblad, Stockholm (SE)

(73) Assignee: SHL Group AB, Nacka Strand (SE)

( * ) Notice: Subject to any disclaimer, the term of this patent is extended or adjusted under 35 U.S.C. 154(b) by 1370 days.

(21) Appl. No.: 12/293,518

(22) PCT Filed: Feb. 26, 2007

(86) PCT No.: PCT/EP2007/051781
§ 371 (c)(1),
(2), (4) Date: Dec. 2, 2008

(87) PCT Pub. No.: WO2007/107431
PCT Pub. Date: Sep. 27, 2007

(65) Prior Publication Data
US 2009/0293870 A1      Dec. 3, 2009

Related U.S. Application Data

(60) Provisional application No. 60/743,604, filed on Mar. 21, 2006.

(51) Int. Cl.
*A61M 15/00* (2006.01)
*A61M 5/00* (2006.01)
(Continued)

(52) U.S. Cl.
CPC ....... *A61M 5/31551* (2013.01); *A61M 15/0065* (2013.01); *A61M 15/0066* (2014.02); *A61M 15/0076* (2014.02); *A61M 5/20* (2013.01); *A61M 5/24* (2013.01); *A61M 5/31556* (2013.01); *A61M 5/3157* (2013.01); *A61M 5/31583* (2013.01); *A61M 5/31593* (2013.01); *A61M 15/08* (2013.01); *A61M 2005/2013* (2013.01); *A61M 2005/3125* (2013.01); *A61M 2005/3126* (2013.01); *A61M 2205/583* (2013.01); *A61M 2205/585* (2013.01)
USPC ................ 128/203.15; 128/203.12; 604/246; 604/71; 604/97.03

(58) Field of Classification Search
USPC ......... 604/211, 207, 181, 131, 187, 208, 209, 604/246, 134, 135, 136; 128/203.12, 919, 128/200.11, 200.12, 200.14, 200.17, 128/200.24, 200.22, 203.15, 205.23
See application file for complete search history.

(56) References Cited

U.S. PATENT DOCUMENTS 4,498,904 A * 2/1985 Turner et al. .................. 604/211
5,582,598 A * 12/1996 Chanoch ....................... 604/208
(Continued)

FOREIGN PATENT DOCUMENTS

WO      97/36626 A      10/1997
WO      99/64092 A      12/1999
(Continued)

OTHER PUBLICATIONS

PCT International Search Report, mailed Jun. 19, 2007, in connection with International Application No. PCT/EP2007/051781.

(Continued)

*Primary Examiner* — Annette Dixon
(74) *Attorney, Agent, or Firm* — Piedmont Intellectual Property

(57) ABSTRACT

A device to be used with a medical administration device includes administration driver for administrating a prescribed dose of medicament; and a mechanical dose setter for setting a prescribed dose of medicament to be administered, including a mechanical indicating member fixedly connected to the administration driver for indicating the prescribed set dose. The device includes a mechanical dose information device for registering the prescribed dose of medicament to be administered including a mechanical information member adjustable to display that the prescribed dose to be administered is correct and inter-connected to said mechanical indicating member such that when the prescribed dose is set, this is indicated positively by indications on the mechanical information member.

19 Claims, 6 Drawing Sheets

(51) Int. Cl.
*A61M 5/315* (2006.01)
*A61M 5/20* (2006.01)
*A61M 5/24* (2006.01)
*A61M 15/08* (2006.01)
*A61M 5/31* (2006.01)

(56) References Cited

U.S. PATENT DOCUMENTS

| | | | |
|---|---|---|---|
| 5,697,916 A * | 12/1997 | Schraga | 604/207 |
| 5,947,934 A | 9/1999 | Hansen et al. | |
| 6,074,372 A * | 6/2000 | Hansen | 604/211 |
| 6,287,283 B1 * | 9/2001 | Ljunggreen et al. | 604/207 |
| 6,524,280 B2 * | 2/2003 | Hansen et al. | 604/207 |
| 6,582,404 B1 * | 6/2003 | Klitgaard et al. | 604/181 |
| 6,666,849 B1 * | 12/2003 | Marshall et al. | 604/246 |
| 6,945,961 B2 * | 9/2005 | Miller et al. | 604/207 |
| 7,214,213 B2 * | 5/2007 | Michel et al. | 604/207 |
| 7,241,278 B2 * | 7/2007 | Moller | 604/211 |
| 7,736,343 B2 * | 6/2010 | Marshall et al. | 604/207 |
| 7,753,879 B2 * | 7/2010 | Mernoe | 604/131 |

FOREIGN PATENT DOCUMENTS

| | | |
|---|---|---|
| WO | 01/54757 A1 | 8/2001 |
| WO | 03/057285 A | 7/2003 |

OTHER PUBLICATIONS

PCT Written Opinion, mailed Jun. 19, 2007, in connection with International Application No. PCT/EP2007/051781.

* cited by examiner

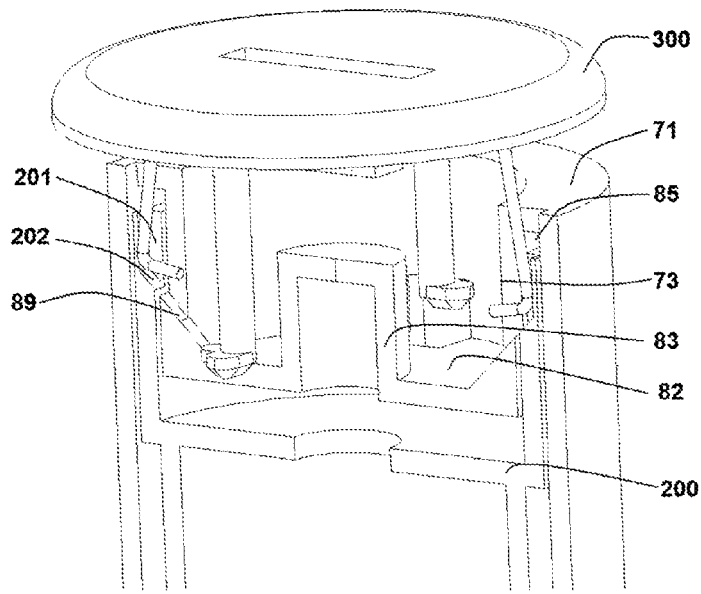
Fig. 6
Fig. 7
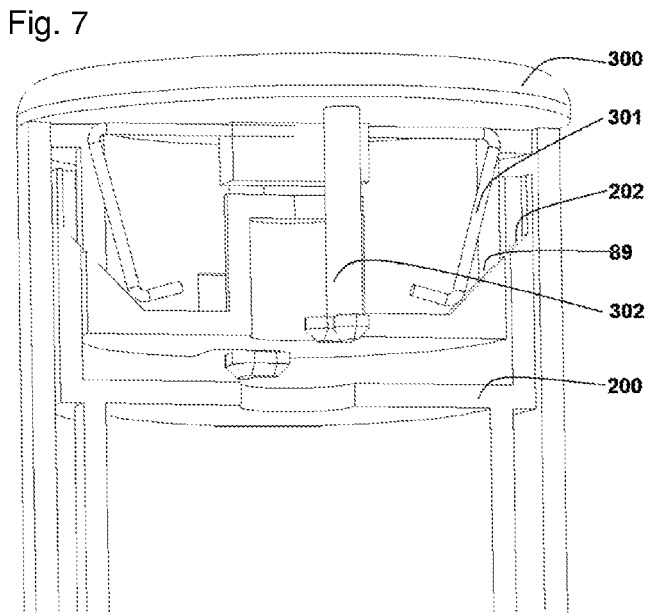

DOSE INFORMATION DEVICE

TECHNICAL FIELD

The present invention relates to a dose information device to be used with a medial delivery device such as an injector, an inhaler or the like.

BACKGROUND ART

There is a large market for a variety of devices for self-administration of medicament and it is growing steadily, mainly because it is cheaper and also more convenient for the patients to handle the administration of medicament themselves instead of having to visit a medial clinic or a doctor in order to have the medicament administered.

Within the field of devices for self-administration there is a variety of devices intended and designed for different types of medicament and different ways of administration, such as inhalers for powder or aerosol driven medicament, nebulizers capable of producing spray of medicament with very fine droplets, injectors for injecting medicament in the body of a patient.

Many of the devices are designed to be able to administer several doses before the device is discarded or needs to be refilled and/or designed to be able to administer doses of medicament that are of different sizes. In the latter case, the device is arranged with some sort of movable part that the patient uses in order to set the correct dose prescribed by the physician. The set dose is often displayed as a digit in a window or for example on a rotatable sleeve of knob, having corresponding indexing means on a fixed part indicating the set dose.

In order to ascertain that the set dose cannot exceed a prescribed dose, a few devices have been developed.

One example of such a device is disclosed in patent application no. WO 99/64092, which describes a device having a knob for setting a certain dose having a scale that displays the different doses to be set. A corresponding indicator is arranged on the housing of the device indicating the set dose. The device is further arranged with an annular member that fits on to the knob and can be rotationally positioned so that, when fitted, a projection comes in contact with the indicator when the correct dose is set. This known dose setting limiter can only be applied to pencil-shaped injection devices of the type having the dose setting knob placed at the rear end of the pen and a stationary raised stud indicating the zero mark of the scale.

The patent application no. WO 01/54757 discloses another device having a dose setting limiter, which prevents that a set dose exceeds the prescribed dose. This dose setting limiter can only be applied to the new generation of very short injection devices e.g. known from U.S. Pat. No. 5,947,934.

Even though these devices function as to limit the risk of setting a too large dose, they have the drawback of being difficult to handle if other dose quantities are to be set and/or including parts that are either rather bulky or not user-friendly.

DISCLOSURE OF INVENTION

The aim of the present invention is to provide a dose information device that indicates when the prescribed dose is set before administration of the medicament.

This aim is solved by a device according to independent claim 1. Preferable embodiments are subject of the dependent claims.

According to a main aspect of the invention it is characterized by a device to be used with a medial administration device, which administration device comprises administration drive means for administrating a prescribed dose of medicament; mechanical dose setting means for setting a prescribed dose of medicament to be administered, including a mechanical indicating member (76) fixedly connected to said administration drive means (84) for indicating the prescribed set dose, wherein said device comprises mechanical dose information means for registering the prescribed dose of medicament to be administered including a mechanical information member adjustable to display that said prescribed dose to be administered is correct, and inter-connected to said mechanical indicating member such that when the prescribed dose is set, this is indicated positively by indications on said mechanical information member.

According to another aspect of the invention it is characterised in that said dose setting means is arranged to rotate, during the setting of the prescribed dose, until the prescribed dose is visible in a dose window and said dose information member is arranged to rotate, during the registration of the prescribed dose, until a positive indication is visible in a register information window.

Yet, according to another aspect of the invention it is characterised in that said mechanical dose information means comprises a locking means for locking said dose information member to said dose setting means, before and under the setting and registration of the prescribed dose and for unlocking said dose information member from said dose setting means, after the setting and registration of the prescribed dose.

Further, according to another aspect of the invention it is characterised in that the dose setting means is arranged with a ratchet and a protrusion arranged to interact with pawl(s) and a protrusion respectively, arranged on said dose information member, for stopping counter-clockwise rotation of the dose setting means during the setting of the registered dose; and for stopping clockwise rotation of the dose setting means after the setting of the registered dose.

Yet, according to another aspect of the invention it is characterised in that said mechanical indicating member is arranged to rotate, during administration of medicament, from a position where the correct prescribed dose is visible, to a position where it is indicated that the correct dose is given, and that said dose information member during administration of medicament, rotates from a position where it is indicated positively that the correct prescribed dose is set, to a position indicating the dose to be set for the subsequent dose delivery.

The benefits of the present invention are several. With the use of a dose information means, it is possible for the user to indicate once the proper prescribed dose to be delivered, which is done the first time the medial administration device is used. For any subsequent dose, because of the inter-connection between the dose setting member and the dose information means, when rotating the dose setting means, the dose information member will indicate positively when the correct prescribed dose is set. The user thus does not have to remember the correct dose for further dose deliveries, because this is indicated by the dose information means.

The dose information member could either display or indicate the actual dose quantity when the dose is to be set, and give a positive indication when this dose is reached by the dose setting means, or could indicate, for example when the dose setting means is rotatable to set the required dose, that the dose setting means should be rotated in either direction for reaching the proper prescribed dose.

Preferably the dose information member is a drum interconnected with the dose setting means, which in turn could be a part of the housing of the medicament delivery device, and connected to for example a plunger rod movable inside the housing during delivery. The movement of the plunger rod thus affects and rotates the dose setting indications as well as the dose information.

The present invention could be used with a number of medial delivery devices that are capable of providing a number of different set doses.

These and other aspects of and advantages with the present invention will become apparent from the following detailed description and from the accompanying drawings.

BRIEF DESCRIPTION OF DRAWINGS

In the following detailed description of the invention, reference will be made to the accompanying drawings of which, FIGS. 1a and b show views partially in cross-section of a medical device intended to comprise a device according to the present invention.

FIG. 6 shows a detailed view of the locking means of FIG. 5 when said locking means is in a released position, FIG. 7 shows a detailed view of the locking means of FIG. 5 when said locking means is in an inserted position.

DETAILED DESCRIPTION OF THE INVENTION

The present invention is intended to be arranged in a medical administering device such as an inhaler or an injector.

Figure 1A:
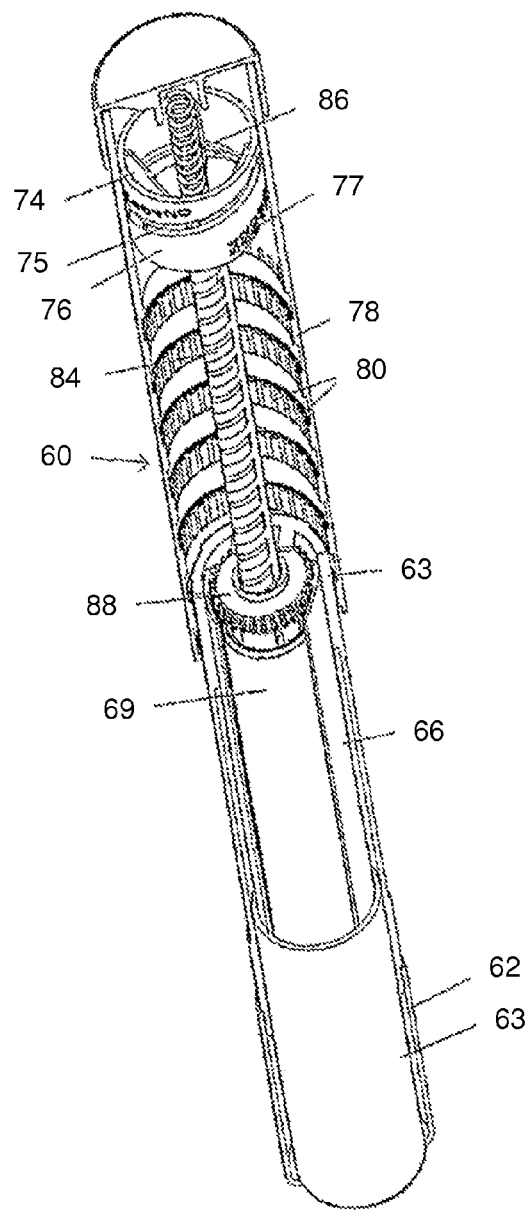
Figure 1B:
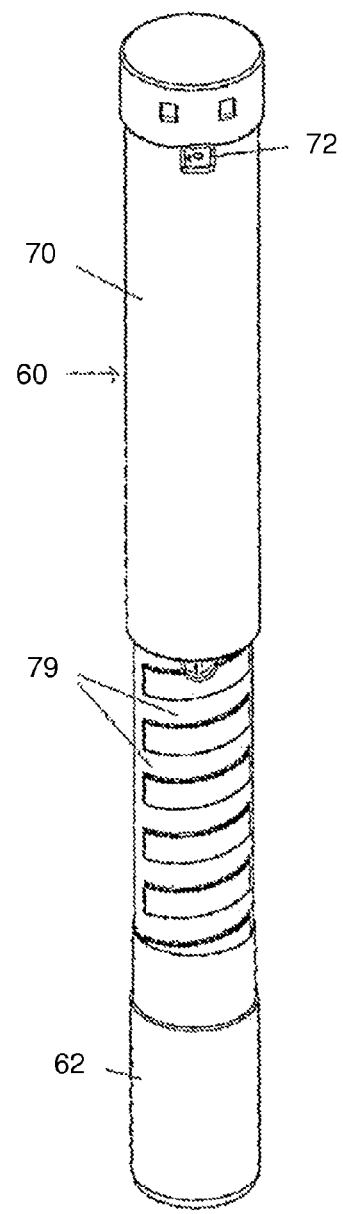

FIG. 1 shows an example of a device suitable to have the present invention. It shows a delivery device 60, comprising in its proximal part a cartridge housing 66 comprising a cartridge 69. The cartridge 69 is intended to be filled with the liquid medicament to be administered to the patient and the delivery device is thus provided with means in order to be connected to a suitable medicament administrating member, such as a needle for the injection of a liquid medicament into the body of the patient, wherein the liquid can have a low as well a high viscosity, bit can also be for instance be a mouth or nasal piece, which the patient pits in his mouth or nose, respectively, whereby a metered dose of medicament is inhaled by the patient when the delivery device is set in a medicament delivery state, which will be described in further detail below. The medicament administering member can also be a member that introduces the liquid medicament to the eye of the patient, such as a suitable nozzle that sprays the medicament to the eye, or a member that introduces the medicament to the eye in the form of droplets. Naturally, a nozzle as a medicament administrating member can also be used in order to spray the medicament onto the skin of the patient.

The delivery device 60 is further in the shown embodiment provided with a needle shield 63, the proximal end of which extends beyond the proximal ends of the cartridge components in order to protect the needle. For further protection of the delivery device, said device may also in its proximal end be provided with removable cap 62. The distal end of the needle shield is provided with inward protruding stopper means, the function of which will be described in further detail below.

The distal part of the delivery device comprises a mechanical dose setting means in the form of a back cover 70 provided with a dose window 72. In the interior distal part of the back cover is a mechanical indicating member in the form of a hollow dose setting drum 76 arranged. The dose setting drum 76 is provided with a through going slot 75 arranged in a helical-formed pattern along the surface of the dose setting drum. The back cover is further in its distal part provided with an inward protruding pin (not shown) arranged to engage and run along the slot 75 of the dose setting drum. Moreover, the external surface of the dose setting drum is circumferentially provided with for instance numerical indicators 77 which are visible for the user through a dose window 72, as described further below. The window 72 can optionally be provided with a suitable lens or the like, in order to enlarge the dose indicators for the user.

The interior surface of the back cover is provided with a thread 78 in order to be screw threaded on the proximal part of the device. The exterior surface of the proximal part of the device is thus also provided with a thread 79 that is adapted to engage the thread 78. The helical-formed configuration of the slot 75 in the dose setting drum 76 consequently corresponds to the pitch of grooving, or screw pitch, of the threads 78, 79. The thread 78 is further provided with equally distributed recesses 80, which correspond to at least one protrusion 81 on the exterior of the proximal part of the device.

An administration drive means in the form of a screw threaded elongated plunger rod 84 is provided in the interior of the delivery device, running along the longitudinal axis of said device. The proximal end of the plunger rod is in contact with a piston (not shown) sealingly and slidably provided inside the cartridge 69. The plunger rod 84 is provided as a hollow member and the hollow interior of the plunger rod is provided with an energy accumulating member in the form of a helical plunger rod spring 86. The distal end of the helical spring 86 is in contact with the inner distal end of the back cover 70 and the proximal end preferably against the inner proximal end surface of the plunger rod 84. The plunger rod 84 is further fixedly connected to the dose setting drum 76 by means of inner connecting means 74.

The plunger rod 84 is adapted to be screwed into the cartridge housing 66 and is further adapted to be housed within a wheel 88 that is provided in the interior of the device 60 distal to the distal end of the cartridge housing. The interior part of the cartridge housing 66 that constitutes an entrance for, and is adapted to engage, the plunger rod is thus provided with a thread that has a pitch of grooving, i.e. a screw pitch, that corresponds to thread of the plunger rod. The threads 78 and 79, the thread in the interior of the cartridge housing, the thread of the plunger rod and as a logical consequence the helical formed configuration of the slot 75, all have the same predetermined pitch of grooving, or screw pitch. The wheel 88 is adapted to be in rotating state and in a non-rotating state and is therefore provided with protruding teeth, which teeth are adapted to engage the stopper means of the needle shield 63. That is, when the delivery device 60 of the third embodiment is in a non-medicament delivery state, a stopper means is provided in between two protruding teeth, holding the wheel in a non-rotating state, as will be described in further detail below. The interior of the wheel 88 is further provided with means that corresponds to the thread on the plunger rod, so that when the wheel 88 is in the non-rotating state, the plunger rod is prevented from rotating. Thus, when the wheel 88 is released for rotation, the plunger can be rotated and screwed into the cartridge housing. The means in the interior of the wheel 88, is thus also adapted so that the wheel can travel along the longitudinal axis of the plunger rod. The interior of the wheel is thus provided with inwardly protruding means 92 that engages longitudinal extending means 91 on the plunger rod.

Before use, the cap 62 is removed from the device 60 and a suitable medicament administrating member is attached to the cartridge retainer, such as a needle. Then the dose is set in a first dose delivery step by rotating the back cover 70 clockwise. When rotating the back-cover, the pin will run along the slot 75 of the dose setting drum 76, and the entire back cover will rotate towards the proximal end of the device 60 as the thread 78 is in engagement with the thread 79. As the back cover 70 moves towards the proximal end of the device, the recesses 80 of the thread 78 slide over the corresponding protrusions 81. Each time a recess 80 slides over such a corresponding protrusion 81, the dose is increased by one step and the set dose is visible for the user of the device through the dose window 72 by the numerical indicators provide on the dose setting drum 76. If the dose is set to high, the user can easily rotate the back cover counter-clock wise and adjust the set dose. It is also possible to provide the device with means (not shown) that sets a certain dose as a default dose value, for instance by providing the slot in the dose setting drum with a stopper means at a predetermined position that prevents the pin from running along said slot a longer distance than the distance that correspond to the default dose.

As the back cover moves in steps towards the proximal end of the device 60, also the plunger rod spring 86 in the interior of the plunger rod 84 is compressed and step-wise accumulates a spring force corresponding to the predetermined distance that the back cover 70 moves towards the proximal end of the device 60. The higher dose set, the greater spring force accumulated in the spring 86.

The delivery device 60 is now ready to be set in a medicament delivery state. This is accomplished by pushing the needle shield 63 towards the distal end of the delivery device, preferably by pushing the proximal end of the needle shield 63 against the patient's skin at the medicament delivery site. When the needle shield moves towards the distal end of the delivery device, the stopper means 65 of the needle shield come out of engagement with the teeth of the wheel 88, as seen in FIG. 1a. Due to the accumulated spring force in the plunger rod spring 86 during the first dose delivery step, the plunger rod will now, provided with the force from the spring 86, be screwed into the cartridge housing and moves thus towards the proximal end of the device. Since the proximal end of the plunger rod is in contact with the piston sealingly provided inside the cartridge 69, said piston will move a predetermined distance towards the proximal end of the cartridge 69 and deliver the set volume dose. The predetermined distance that the piston 87 moves inside the cartridge, and thus the force acting on the piston, is determined by the spring force accumulated in the plunger rod spring when the dose is set as well as by the threaded design of the threaded components of the device, i.e. the threads 78 and 79, the thread in the interior of the cartridge housing and the thread on the plunger rod. The finer the pitch of grooving, or screw pitch, of the threaded components, the higher degree of accuracy will be achieved and the lower the force acting on the piston. The device 60 is designed in accordance with the cartridge so that the movement of the piston the predetermined distance towards the proximal end of the cartridge will correspond to the delivery of the dose set in the first dose delivery step.

During dose delivery, when the plunger rod 84 is forced into the cartridge housing, the wheel 88 is rotated along with the rotating plunger rod and travels along its longitudinal axis. The dose setting drum 76 is rotated and moves along with the downwards rotating plunger rod due to the connecting means 74, whereupon the dose volume to be delivered is visible for the user through the dose window 72 and counts down until the entire dose is delivered. If the cartridge is emptied before the entire dose is delivered, the dose remaining to be taken is shown in the window. The back cover will however, stay at its current position and the device thus becomes shorter every time it is used. The exterior surface of the proximal part of the device, can thus be provided with further dose indicator means (not shown), that by means of the current position of the back cover indicates the remaining doses, i.e. the remaining amount of medicament, in the cartridge.

Figure 2:
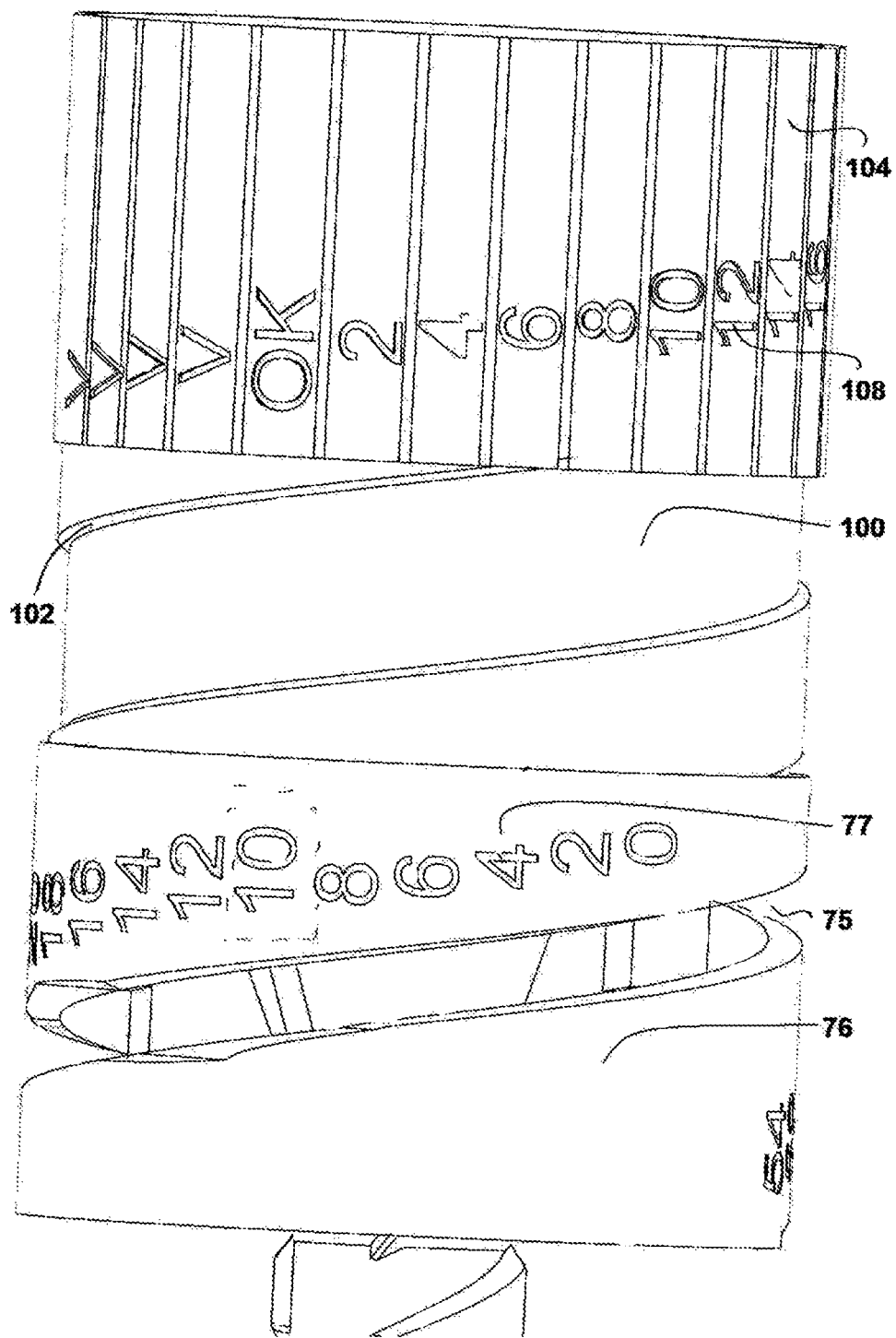
FIG. 2 shows a detailed view of a component of the device according to a first embodiment of the present invention.
Figure 3:
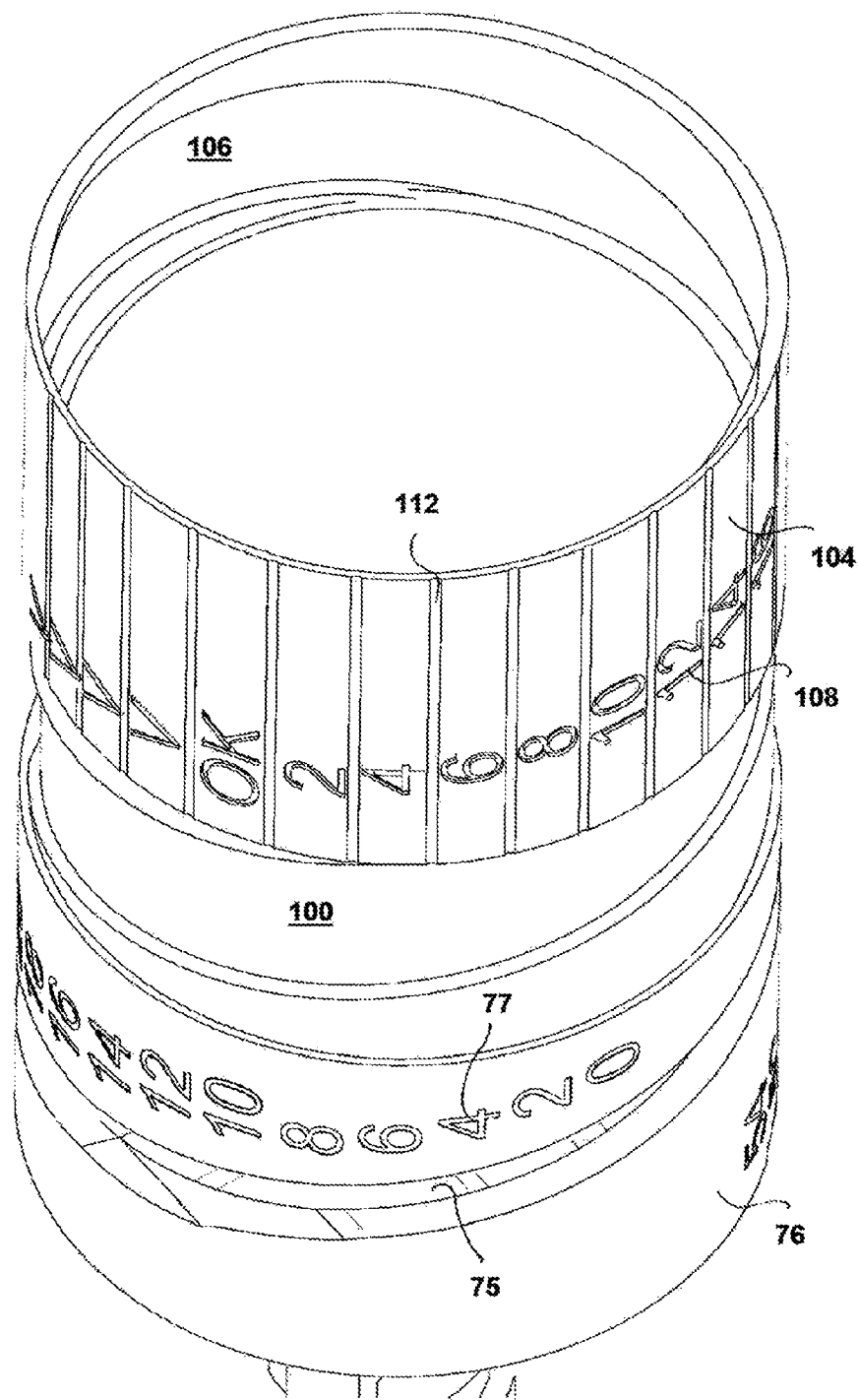
FIG. 3 shows another view of the component of FIG. 2.
Figure 4:
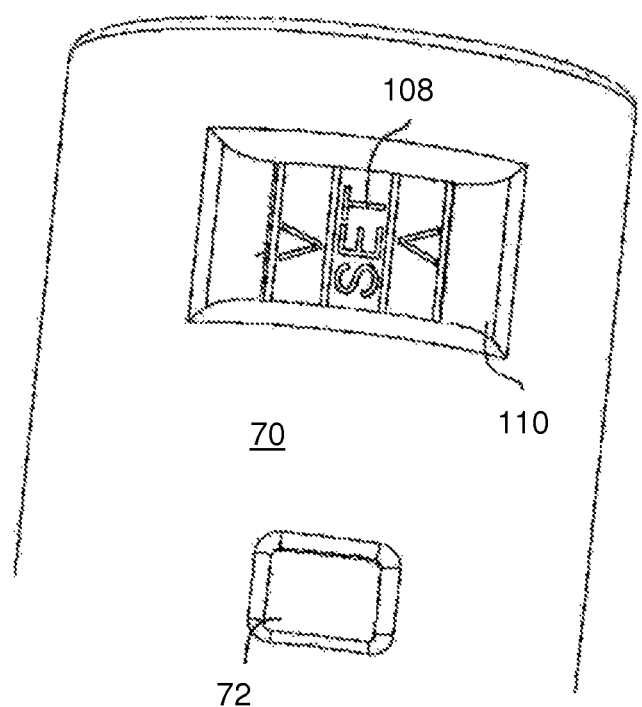
FIG. 4 shows a detailed view of a medial device comprising the present invention.

According to the present invention, FIG. 2 shows a first embodiment of a dose information means arranged to interact with the dose setting means 70 of the described delivery device. The rotating dose setting drum 76, with the through-going slot 75 and numerical indicators 77, is in this case longer, i.e. has a hollow cylindrical part 100 attached to the upper end surface of the dose setting drum. The cylindrical part 100 is arranged with helical threads 102. In order to accommodate the cylindrical part, the back cover 70 is also made longer, FIG. 4. Around the cylindrical part a mechanical dose information means, in the embodiment shown a dose information member 104 is arranged, having corresponding threads 106 on its inner surface. The dose information member is arranged with indications 108 around its outer surface; such as for example dose quantity. The back cover 70 is further arranged with a register information window 110, in which the indications are visible.

When a certain dose is to be set and this dose is to be "registered" by the dose information member 104, the back cover 70 is rotated clock-wise in a manner described above until the proper, prescribed dose is visible through the dose window 72. As seen in FIG. 2, as an example, the prescribed dose could be 10. Now the proper, prescribed dose is to be registered by the dose information member 104. The register information window 110 is in this respect so large that it is possible to insert a finger and to rotate the drum until the corresponding dose indication is shown in that window. It is also conceivable that a second window is arranged on the opposite side of the back cover 70 in order to enhance the rotation of the dose information member.

In order to facilitate the rotation of the dose information member 104 it is preferably arranged with grooves 112 or other grip-enhancing means. The rotation of the dose information member causes it to move towards the proximal end of the device due to the threading 102 between the cylindrical part and the dose information member. The indications 108 of the dose information member correspond in placing the indications of the dose setting drum 76. As seen in FIG. 2 the dose information member 104 is rotated until the indication "OK" is visible in the register information window 110.

When the dose subsequently is delivered, the dose setting drum 76 is rotated as described above until the entire dose is delivered whereby the dose setting drum counts down to zero. Because of the connection with the dose information member 104, it is also rotated, and because of the indications of the dose information member, the proper, prescribed dose is shown in the register information window when the entire dose is delivered, in the shown case "10". Thus, the next time the patient is to set a proper dose, the actual dose to be set is shown in the dose information window. The patient is thus provided with a first indication as to which dose to set, and when rotating the dose setting drum, obtains a second indication that the proper dose is set in that "OK" is shown in the dose information window.

Instead of having dose quantities displayed in the dose information window, the dose information member can be arranged with a positive indication, like "OK", a happy face, an arrow pointing towards the front of the device, or any characteristic indication, and for example, arrows on both sides of this positive indication pointing towards this indication. This will show the user, when setting a dose, in which direction he or she has to rotate the back cover in order to arrive at the proper dose.

Figure 5:
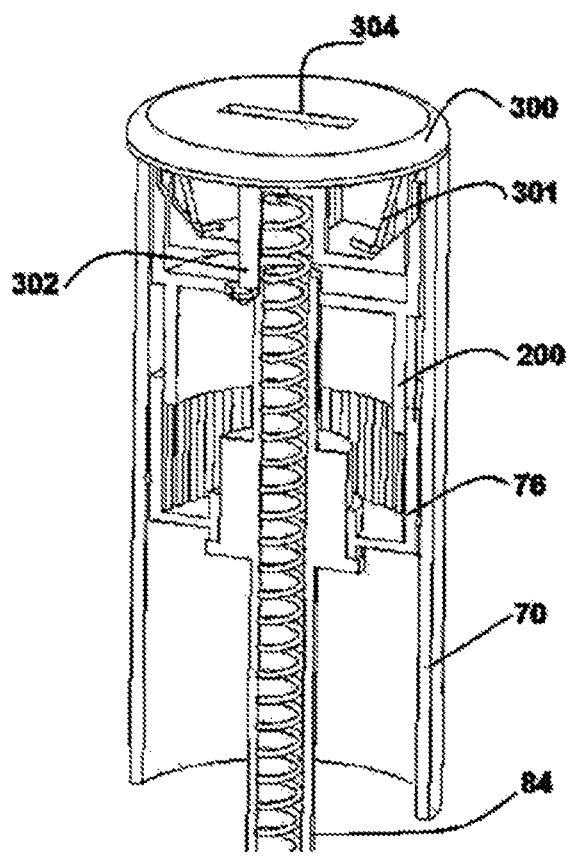
FIG. 5 shows the device according to a second embodiment of the present invention, partly in cross-section having a locking means.

According to the present invention, FIG. 5 shows a second embodiment of a dose information means arranged to interact with the dose setting means 70 of the delivery device. The rotating dose setting drum 76, with the through-going slot 75 and numerical indicators 77, has in this case a friction ratchet (not shown) arranged on the upper end inner surface of said dose setting drum 76. Inside said inner surface, a dose information member 200 having an equivalent friction ratchet on its lower end otter surface is arranged. As seen in FIG. 6, said dose information member 200 is also arranged with two slots 201 on its upper end inner surface and wherein said slots 201 comprise sloping edges 202. Further, said dose information member 200 is arranged with indications around its otter surface and the back cover 70 is also arranged with a register information window 110, in which the indications are visible. The indications can be a positive indication, like "OK", "SET", a happy face, an arrow pointing towards the front of the device, or any characteristic indication, and arrows on both sides of this positive indication pointing towards this indication.

In this second embodiment, the back cover 70 has been modified at its upper end as shown in FIG. 6. The distal end of the back cover is arranged with a wall 71 which extends axially a certain distance; a wall 73 which extends longitudinally a certain distance from the wall 71 towards the proximal end forming a slot 85; and a wall 82 which extends axially a certain distance from the wall 73 forming a closed bulge 83 wherein the distal end of the helical spring 86 is supported. In said slot 85, between the wall 73 and the inner surface of the back cover 70, the upper end of the dose information member 200, is rotatably arranged.

In order to facilitate the rotation of the dose information member 200 under the setting and registration of the prescribed dose, said dose information means comprises a locking means 300 arranged to be movable to a released and to an inserted position. Said means 300 comprises steel springs 301, locking pins 302 and a release slot 304. For this purpose, the wall 71 of the back cover 70 is also arranged with slots wherein the steel springs can be inserted and slidable through sloping edges 89 of the wall 73. Moreover said sloping edges 89 match and have the same inclination of the sloping edges 202 of the dose information member 200.

When a certain dose is to be set and this dose is to be "registered" by the dose information member 200, the locking means must be positioned in a released position as shown in FIG. 6, wherein the steel springs 301 make contact with the slots 201 of the dose information member 200 and with the wall 73 of the back cover 70. Then the back cover 70 is rotated clockwise wherein the dose information member 200 is also rotated with the indication e.g. "OK", "SET" visible in the register information window 110 until the proper, prescribed dose is visible through the dose window 72. Now, the locking means 300 must be positioned in an inserted position through pressing said means 300 towards the proximal end so that the locking pins 302 lock the locking means to the wall 82 of the back cover 70 and the steel springs 301 slides over the sloping edge 202, 89; wherein said steel springs remain supported on the sloping edged 89, see FIG. 7. Then, the dose information member 200 is free from the back cover 70 and rotates together with dose setting drum 76 when the set and registered dose is delivered.

When the dose subsequently is delivered, the dose setting drum 76 is rotated as described above until the entire dose is delivered whereby the dose setting drum counts down to zero. Because of the connection with the dose information member 200, it is also rotated, and because of the indications of the dose information member, the proper, prescribed dose is set the next time the patient is to set the prescribed dose, when the positive indication is shown in the register information window 110.

Heretofore, with the above mentioned embodiments, after a prescribed dose has been registered, the patient/user has the freedom to rotate the dose setting means to a higher or lower dose that the prescribed dose though the indications of the dose information member. Since, after a prescribed dose has been registered, the dose setting means 70 and the dose information member (104; 200) is always rotated to the sane amount, the prescribed dose, before each delivery, a third embodiment will be described, wherein the patient will not have the above mentioned freedom.

Figure 8:
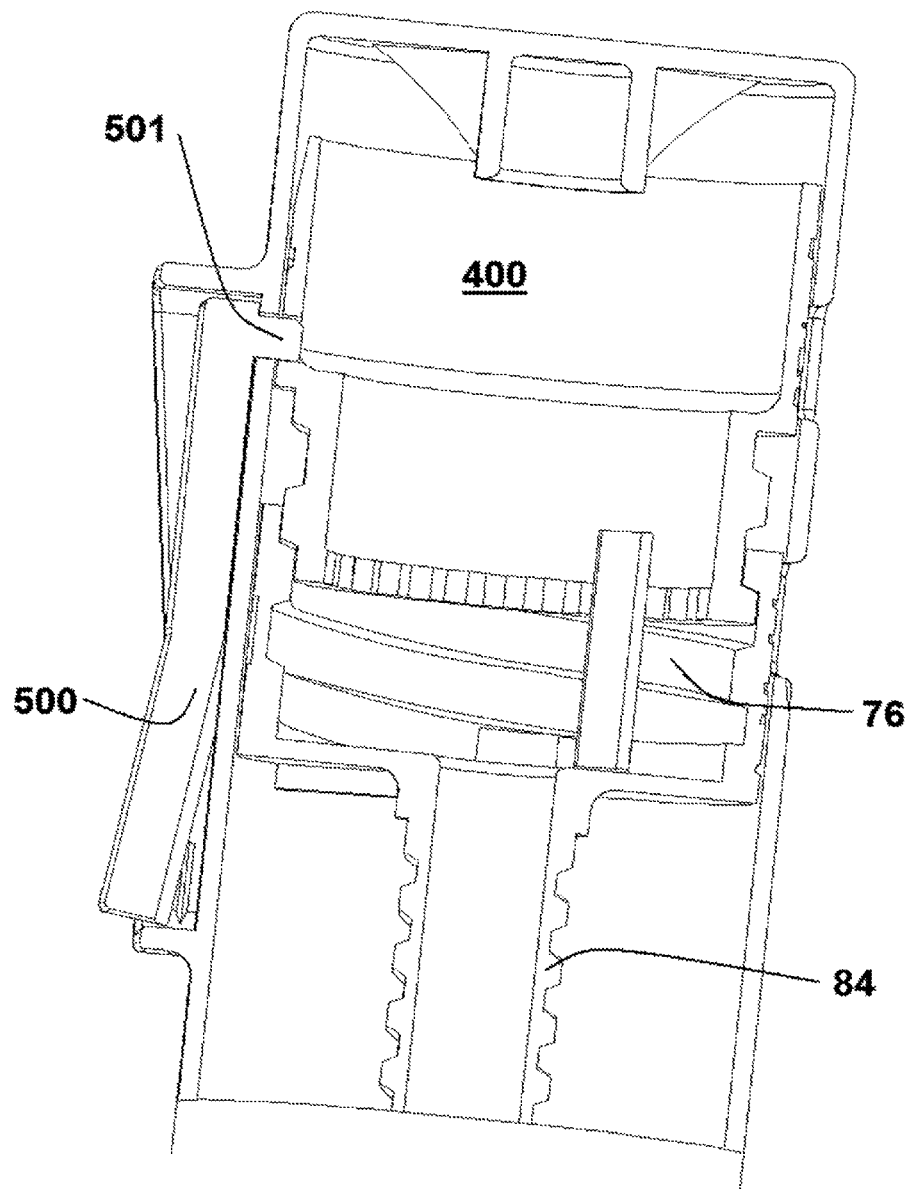
FIG. 8 shows the device according to a third embodiment of the present invention, partly in cross-section having a locking means.

According to the present invention, FIG. 8 shows a third embodiment of a dose information means arranged to interact with the dose setting means 70 of the delivery device. The rotating dose setting drum 76, with the through-going slot 75 and numerical indicators 77, has also in this third embodiment a friction ratchet (not shown) arranged on the upper end inner surface of said dose setting drum 76. Inside said inner surface, a dose information member 400 having an equivalent friction ratchet on its lower end otter surface is arranged. Moreover, inside the inner surface of said dose setting drum 76 and under its friction ratchet, a set of splines is arranged for locking said information member 400 to said dose setting drum 76. Further, said dose information member 400 is arranged with indications around its otter surface and the back cover 70 is also arranged with register information window 110, in which the indications are visible. The indications can be a positive indication, like "OK", "SET", a happy face, an arrow pointing towards the front of the device, or any characteristic indication, and arrows on both sides of this positive indication pointing towards this indication. Moreover, said dose information member 400 comprises at least one pawl (not shown) arranged on the upper end outer surface of the dose information member 400.

In this third embodiment, a ratchet (not shown) on the inner surface of the back cover 70 is arranged to interact with the pawl(s) of the dose information member 400.

In order to facilitate the rotation of the dose information member 400 under the setting and registration of the prescribed dose, said dose information means comprises locking means 500 slidable and switchable arranged on the surface of the back cover 70, as shown in FIG. 8. Said locking means 500 comprises a connecting pin 501 for locking said dose information member 400 to said back cover 70 when said locking means is/are switched. Thereafter, said locking means is/are slidable actuated for unlocking said dose information member 400 from said dose setting drum 76, and for bringing said ratchet on the inner surface of the back cover 70 out of contact with the pawl(s) of the dose information member 400. Then, the setting and registration of the prescribed dose can be done through rotating the back cover 70 clockwise wherein the dose information member 400 is also rotated with the indication e.g. "OK", "SET" visible in the register information window 110 until the proper, prescribed dose is visible through the dose window 72.

After the setting and registration of the prescribed dose, said locking means 500 are slidable actuated for locking said dose information member 400 to said dose setting drum 76, and for bringing said ratchet on the inner surface of the back cover 70 in contact with the pawl(s) of the dose information member 400. Thereafter, said locking means 500 is/are switched back for unlocking said dose information member 400 from said back cover 70.

When the dose subsequently is delivered, the dose setting drum 76 is rotated until the entire dose is delivered whereby the dose setting drum counts down to zero. Because of the connection with the dose information member 400, it is also rotated, and because of the indications of the dose information member, the proper, prescribed dose is set the next time the patient is to set the prescribed dose, when the positive indication is shown in the register information window 110.

The dose information member (104; 200; 400) and the dose setting means 70 are each arranged with a protrusion (not shown) wherein said protrusions are arranged for stopping clockwise rotation of the dose setting means 70, during the setting of the registered dose.

Thus, with this third embodiment, when the patient/user intend to set the registered prescribed dose again, he/she needs only to rotate the dose setting means 70 clockwise until it stops and the positive indication is also shown in the register information window 110. The patient/user cannot rotate the dose setting means 70 counter-clockwise due to the design of ratchet on the inner surface of the back cover 70 and the pawl(s) of the dose information member 400.

It is to be understood that the present invention may be modified in a number of ways in order to arrive at the present invention. For example the dose information wheel may be connected to the dose setting wheel in other ways to perform the desired function.

The invention claimed is:

1. A device to be used with a medical administration device, the device comprising a drive device for administering a prescribed dose of medicament and a mechanical dose setting device for setting a prescribed dose of medicament to be administered, the mechanical dose setting device being rotatable in relation to the drive device, and a mechanical indicating member for indicating the set prescribed dose fixedly connected to the drive device, the device further comprising:
   a mechanical dose information member that is movably inter-connected to the mechanical indicating member and that includes a plurality of indications for registering the set prescribed dose such that when the prescribed dose is set is indicated by a positive indication on the dose information member.

2. The device of claim 1, wherein the dose setting device comprises a dose window and a register information window.

3. The device of claim 2, wherein the dose setting device is arranged to be rotated relative to the indicating member during setting of the prescribed dose until the prescribed dose is visible in the dose window, and the dose information member is arranged to be rotated relative to the dose setting device and the indicating member during registration of the prescribed dose until the positive indication is visible in the register information window.

4. The device of claim 3, wherein the dose information member includes a grip-enhancing device for registering the set prescribed dose after setting of the prescribed dose.

5. The device of claim 2, wherein the dose information member comprises a locking device for locking the dose information member to the dose setting device before and during setting and registration of the prescribed dose and for unlocking the dose information member from the dose setting device after setting and registration of the prescribed dose.

6. The device of claim 5, wherein the locking device is switchable and slidable on a surface of the dose setting device for locking the dose information member to the indicating member after setting and registration of the prescribed dose and for unlocking the dose information member from the indicating member before setting and registration of the prescribed dose.

7. The device of claim 6, wherein a ratchet on an inner surface of the dose setting device is arranged to be in contact with at least one pawl on an outer surface of the dose information member when the dose information member is locked to the indicating member and to be out of contact with the at least one pawl when the dose information member is unlocked from the mechanical indicating member.

8. The device of claim 7, wherein the ratchet and the at least one pawl interact to stop counter-clockwise rotation of the dose setting device during setting of the registered dose.

9. The device of claim 2, wherein each of the dose information member and the dose setting device has a protrusion, and the protrusions are arranged to stop clockwise rotation of the dose setting device during setting of the registered dose.

10. The device of claim 2, wherein the indicating member is arranged to rotate, during administration of medicament, from a position in which a correct prescribed dose is visible to a position in which it is indicated that the correct prescribed dose is given, and the dose information member rotates, during administration of medicament, from a position in which it is indicated positively that a correct prescribed dose is set to a position indicating the dose to be set for subsequent dose delivery.

11. The device of claim 1, wherein the dose information member comprises a locking device for locking the dose information member to the dose setting device before and during setting and registration of the prescribed dose and for unlocking the dose information member from the dose setting device after setting and registration of the prescribed dose.

12. The device of claim 11, wherein the locking device is switchable and slidable on a surface of the dose setting device for locking the dose information member to the indicating member after setting and registration of the prescribed dose and for unlocking the dose information member from the indicating member before setting and registration of the prescribed dose.

13. The device of claim 12, wherein a ratchet on an inner surface of the dose setting device is arranged to be in contact with at least one pawl on an outer surface of the dose information member when the dose information member is locked to the indicating member and to be out of contact with the at least one pawl when the dose information member is unlocked from the mechanical indicating member.

14. The device of claim 13, wherein the ratchet and the at least one pawl interact to stop counter-clockwise rotation of the dose setting device during setting of the registered dose.

15. The device of claim 1, wherein each of the dose information member and the dose setting device has a protrusion, and the protrusions are arranged to stop clockwise rotation of the dose setting device during setting of the registered dose.

16. The device of claim 1, wherein the indicating member is arranged to rotate, during administration of medicament, from a position in which a correct prescribed dose is visible to a position in which it is indicated that the correct prescribed dose is given, and the dose information member rotates, during administration of medicament, from a position in which it is indicated positively that a correct prescribed dose is set to a position indicating the dose to be set for subsequent dose delivery.

17. The device of claim 1, wherein the positive indication on the dose information member includes at least one of a dose quantity, an OK indication, a pictogram, an arrow, and a characteristic indication.

18. A device to be used with a medical administration device, the device comprising a drive device for administering a prescribed dose of medicament and a mechanical dose setting device for setting a prescribed dose of medicament to be administered, the mechanical dose setting device being rotatable in relation to the drive device, and a mechanical indicating member for indicating the set prescribed dose fixedly connected to the drive device, the device further comprising:

a mechanical dose information member that is movably inter-connected to the mechanical indicating member and that includes a plurality of indications for registering the set prescribed dose such that when the prescribed dose is set is indicated by a positive indication on the dose information member;

wherein the dose setting device comprises a dose window and a register information window, the dose setting device is arranged to be rotated relative to the indicating member during setting of the prescribed dose until the prescribed dose is visible in the dose window, and the dose information member is arranged to be rotated relative to the dose setting device and the indicating member during registration of the prescribed dose until the positive indication is visible in the register information window.

19. The device of claim 18, wherein the dose information member includes a grip-enhancing device for registering the set prescribed dose after setting of the prescribed dose.

* * * * *